US012676229B2

(12) United States Patent
Cai et al.

(10) Patent No.: US 12,676,229 B2
(45) Date of Patent: Jul. 7, 2026

(54) ADAPTIVE ULTRASOUND DEEP CONVOLUTION NEURAL NETWORK DENOISING USING NOISE CHARACTERISTIC INFORMATION

(71) Applicant: CANON KABUSHIKI KAISHA, Tokyo (JP)

(72) Inventors: Liang Cai, Vernon Hills, IL (US); Jian Zhou, Vernon Hills, IL (US); Ting Xia, Vernon Hills, IL (US); Zhou Yu, Vernon Hills, IL (US); Tomohisa Imamura, Otawara (JP); Ryosuke Iwasaki, Otawara (JP); Hiroki Takahashi, Nasushiobara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 521 days.

(21) Appl. No.: 17/730,954

(22) Filed: Apr. 27, 2022

(65) Prior Publication Data

US 2022/0367039 A1     Nov. 17, 2022

Related U.S. Application Data

(60) Provisional application No. 63/185,680, filed on May 7, 2021.

(51) Int. Cl.
| | |
|---|---|
| *G16H 30/40* | (2018.01) |
| *A61B 8/00* | (2006.01) |
| *G06N 3/08* | (2023.01) |
| *G06T 5/70* | (2024.01) |

(52) U.S. Cl.
CPC ........... *G16H 30/40* (2018.01); *A61B 8/5269* (2013.01); *G06N 3/08* (2013.01); *G06T 5/70* (2024.01);
(Continued)

(58) Field of Classification Search
CPC ........ G16H 30/40; G16H 30/20; G16H 50/20; A61B 8/5269; A61B 8/4483; A61B 8/488;
(Continued)

(56) References Cited

U.S. PATENT DOCUMENTS

| | | |
|---|---|---|
| 2018/0144214 A1 | 5/2018 | Hsleh et al. |
| 2019/0251668 A1 | 8/2019 | Meyer et al. |

(Continued)

OTHER PUBLICATIONS

Chang ", Two-Stage Convolutional Neural Network for Medical Noise Removal via Image Decomposition", IEEE Transactions on Instrumentation and Measurement, vol. 69, No. 6, Jun. 2020 (Year: 2020).*

(Continued)

*Primary Examiner* — Mekonen T Bekele
(74) *Attorney, Agent, or Firm* — Oblon, McClelland, Maier & Neustadt, L.L.P.

(57)     ABSTRACT

A method and system enable to-be-processed medical image data and its corresponding noise characteristic information to be normalized to resemble noise characteristic information of training data used to train at least one neural network for at least one ultrasound data acquisition mode. After normalizing, this processed medical image data is input into the trained neural network for producing output data used for generating cleaner images. Noise characteristic information can be used directly in training a neural network, generating a trained neural network that can handle medical image data with various noise characteristics.

18 Claims, 8 Drawing Sheets

(52) U.S. Cl.
CPC ............... *G06T 2207/10132* (2013.01); *G06T 2207/20081* (2013.01); *G06T 2207/20084* (2013.01)

(58) Field of Classification Search
CPC ....... A61B 8/58; A61B 8/0883; A61B 8/4488; A61B 8/0833; G06N 3/08; G06N 3/0464; G06N 3/045; G06N 3/09; G06T 5/70; G06T 2207/10132; G06T 2207/20081; G06T 2207/20084; G06T 5/60
See application file for complete search history.

(56) References Cited

U.S. PATENT DOCUMENTS

| | | | |
|---|---|---|---|
| 2020/0065940 A1* | 2/2020 | Tang | G06T 5/70 |
| 2020/0175675 A1* | 6/2020 | Ogino | A61B 5/00 |
| 2020/0295863 A1* | 9/2020 | Pajovic | H04B 1/709 |
| 2020/0401832 A1 | 12/2020 | Peng | |

OTHER PUBLICATIONS

Chang et al., "Two-Stage Convolutional Neural Network for Medical Noise Removal via Image Decomposition", IEEE Transactions on Instrumentation and Measurement, vol. 69, No. 6, pub. Jun. 2020, (Year: 2020).*

Josh Schaefferkoetter et al "Convolutional neural networks for improving image quality with noisy PET data." https://ejnmmires.springeropen.com/articles/10.1186/s13550-020-00695-1. Sep. 21, 2020.

* cited by examiner

1

ADAPTIVE ULTRASOUND DEEP CONVOLUTION NEURAL NETWORK DENOISING USING NOISE CHARACTERISTIC INFORMATION

CROSS-REFERENCE TO CO-PENDING APPLICATION

The present application relates to and claims priority under 35 U.S.C. § 119(e) to U.S. Provisional Patent Application No. 63/185,680 filed on May 7, 2021, the contents of which are incorporated herein by reference.

BACKGROUND

When performing ultrasound imaging, such as ultrasound B-mode or Doppler imaging, noise is a degrading factor. For example, during intrinsic transducer data collection, additional noise is introduced to the IQ (in phase and quadrature) signal. Such noise appears as additional electronic noise, and cannot be easily separated from the true IQ signal. This noise results in degraded medical images, which is undesirable.

SUMMARY

The present disclosure is directed to a medical image processing apparatus comprising: memory storing at least one trained model for denoising medical image data; processing circuitry configured to (1) obtain processed medical image data by normalizing noise characteristic information of the medical image data to resemble noise characteristic information of training data used for training a corresponding trained model of the at least one trained model and (2) input the processed medical image data into the corresponding trained model to obtain output data; and a display control circuitry configured to cause a display unit to display a medical image based on the obtained output data.

In one embodiment, the at least one trained model for denoising medical image data stored in the memory comprises plural trained models, the processing circuitry further comprising processing circuitry configured to choose the corresponding trained model from the plural trained models using system parameters of a system used to collect the medical image data.

In one embodiment, the at least one trained model for denoising medical image data stored in the memory comprises plural trained models, the processing circuitry further comprising processing circuitry configured to choose the corresponding trained model from the plural trained models using a pre-scanning by the apparatus of air.

In one embodiment, the noise characteristic information is depth-specific noise information related to an ultrasound scanner.

In one embodiment, the medical image processing apparatus is an ultrasound scanner. In one embodiment, the ultrasound scanner performs ultrasound B-mode imaging. In another embodiment, the ultrasound scanner performs Doppler ultrasound.

In one embodiment, the medical image data can be IQ data, image data, raw image data, reconstructed image data, or RF data.

The present disclosure is also directed to a medical image processing apparatus comprising: a memory storing a trained model generated by a machine-learning process based on first medical image data, noise characteristic information of the first medical image data, and second medical image data based on the first medical image data, the second medical image data having less noise than the first medical image data; processing circuitry configured to input medical image data into the trained model to obtain output data; and a display control circuitry configured to cause a display unit to display a medical image based on the obtained output data.

In one embodiment, the first medical image data and the noise characteristic information of the first medical image data are used as input learning data, and the second medical image data is used as output learning data.

In one embodiment, the noise characteristic information of the first medical image data is obtained by analyzing system parameters of a system used to collect the first medical image data.

In one embodiment, the noise characteristic information of the first medical image data is obtained by performing a pre-scanning scheme in a system used to collect the first medical image data.

In one embodiment, the processing circuitry is further configured to input noise characteristic information of the medical image data into the trained model.

The present disclosure is also directed to a method comprising: obtaining processed medical image data by normalizing noise characteristic information of medical image data to resemble noise characteristic information of training data used for training a corresponding trained model from at least one trained model; inputting the processed medical image data into the corresponding trained model to obtain output data; and displaying a medical image based on the obtained output data.

One embodiment further comprises choosing the corresponding trained model from the at least one trained model using system parameters of a system used to collect the medical image data, wherein the at least one trained model comprises plural trained models.

One embodiment further comprises choosing the corresponding trained model from the at least one trained model using a pre-scanning by the apparatus of air, wherein the at least one trained model comprises plural trained models.

In one embodiment, the noise characteristic information is depth-specific noise information related to an ultrasound scanner.

In one embodiment, the medical image data is obtained from an ultrasound scanner. In one embodiment, the ultrasound scanner performs at least one of Doppler ultrasound and ultrasound B-mode imaging.

In one embodiment, the medical image data can be IQ data, image data, raw image data, reconstructed image data, or RF data.

DETAILED DESCRIPTION

As previously mentioned, noise is a degrading factor when performing ultrasound imaging. Therefore, it is desirable to denoise the ultrasound IQ (in phase and quadrature) signal, which can improve signal to noise ratio and enable the generation of higher quality images. IQ data will be used as an example in this disclosure, but it should be noted that the signal to be denoised is not limited to data in an IQ format and may be, for example, raw image data, reconstructed image data (e.g., converted from IQ data), and RF data (including the magnitude of the signal).

In ultrasound imaging, noise added to the IQ signal can vary depending on various scan conditions (i.e. data acquisition modes). Examples of scan conditions that can affect the noise added to IQ signals include the depth, transducer probe frequency, analog gain settings, digital gain settings, and more.

Figure 1:
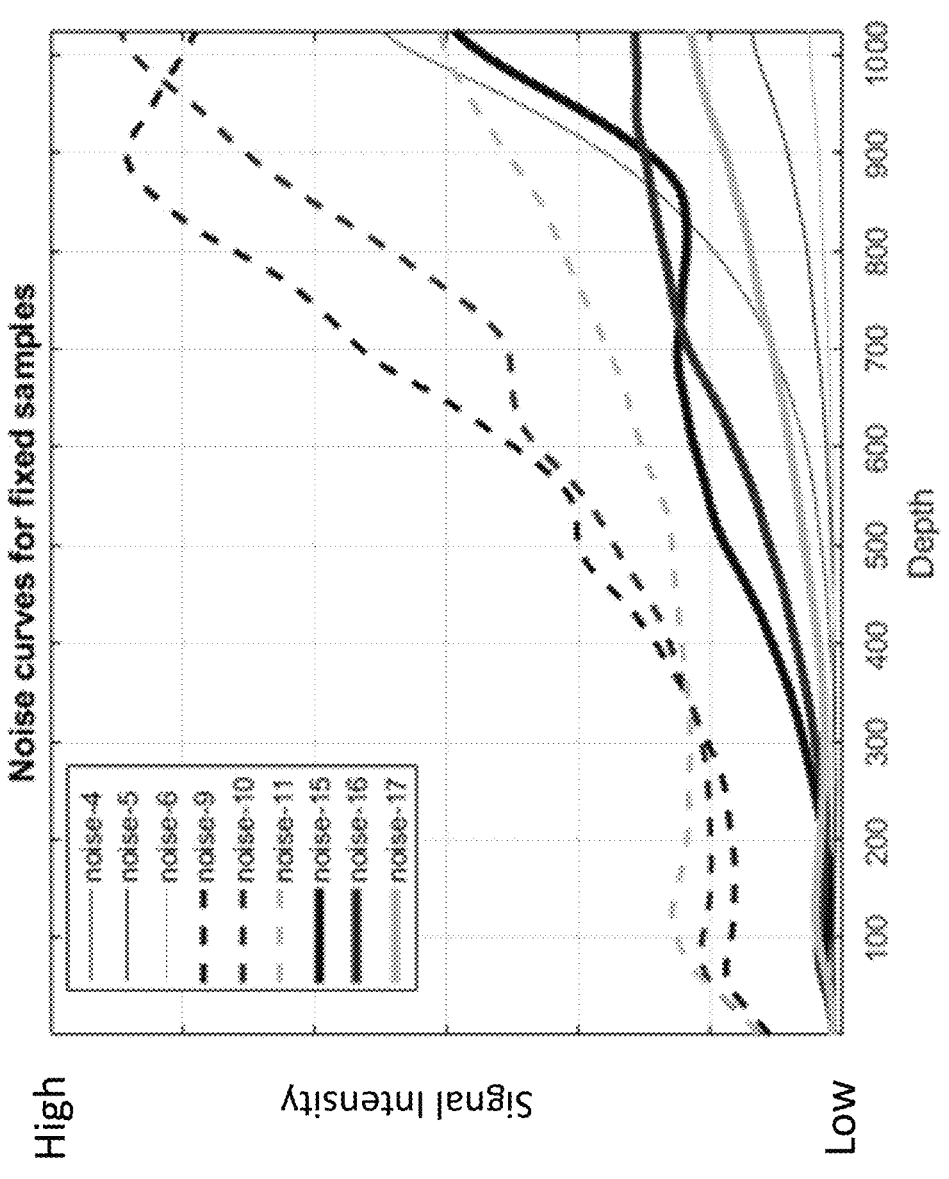
FIG. 1 illustrates noise characteristic information for various data acquisition modes, according to one embodiment of the present disclosure.

FIG. 1 illustrates various IQ noise curves, referred to hereinafter as noise characteristic information, that can be generated according to different data acquisition modes. For example, scanning a patient at a specific location and depth with a transducer probe operating at one frequency can generate noise characteristic information that is different from a scan of the same patient at the exact same location using a transducer probe operating at a different frequency. However, as will be discussed in the present disclosure, such noise characteristic information can be pre-calculated and utilized to generate higher quality ultrasound images, regardless of varying scan conditions by denoising the IQ signals.

Noise characteristic information of one or more scan conditions can be obtained and utilized. In one embodiment, a trained model can be trained using high and low quality image pairs having the same noise characteristic information. Thereafter, to-be-processed medical image data having different noise characteristics can have their noise characteristic information normalized to be similar to the noise characteristic information of images used in training the trained model. This processed medical image data can then be input into the trained model for producing a dataset having denoised IQ signals that can subsequently he used for generating higher quality images.

In another embodiment, a trained model can be trained using low quality images generated under various scan configurations, noise characteristic information of each low quality image, and high quality images based on the low quality images. Thereafter, the trained model can take a low quality image and the low quality image's noise characteristic information as input, and output a higher quality version of the low quality image.

The present disclosure will use ultrasound imaging as an exemplary application, and a neural network as an exemplary trained model. Of course, it can be appreciated that other types of imaging systems and/or trained models can be used in other embodiments.

There are a number of ways to acquire noise characteristic information.

In one embodiment, the noise characteristic information can be determined by system parameters for a particular scan configuration. By considering parameters such as the scan depth, transducer probe frequency, analog gain settings, and digital gain settings, the noise characteristic information can be determined.

In another embodiment for gathering noise characteristic information, a pre-scanning scheme can be performed. The noise characteristic information is depth dependent and based on several factors, such as depth and acquisition settings (e.g., frequency). The pre-scanning scheme can be performed for a particular scan configuration by performing two consecutive purely receive events without ultrasound transmission (e.g., air scan). The data collected by the two consecutive receive events can then be subtracted from each other, thereby generating the noise characteristic information. This enables the noise characteristic information to be generated in real-time.

The noise characteristic information can be depth-specific or across an entire depth of an object being scanned. Noise characteristic information at different depths can have different magnitudes of noise. In the case that the noise characteristic information is depth-specific, only the noise characteristic information related to the specific depth(s) of interest are necessary to perform the techniques discussed herein. For example, if an ultrasound scan is only interested in information at depth 500 to 700, noise characteristic information is only needed for depths between 500 and 700. As another example, if the depth of interest is at 15 centimeters, noise characteristic information is only needed for depths up to 15 centimeters. Alternatively, if a region of interest is limited to a particular range (e.g., 1 to 3 cm), then noise characteristic information is only needed for that range.

Figure 2:
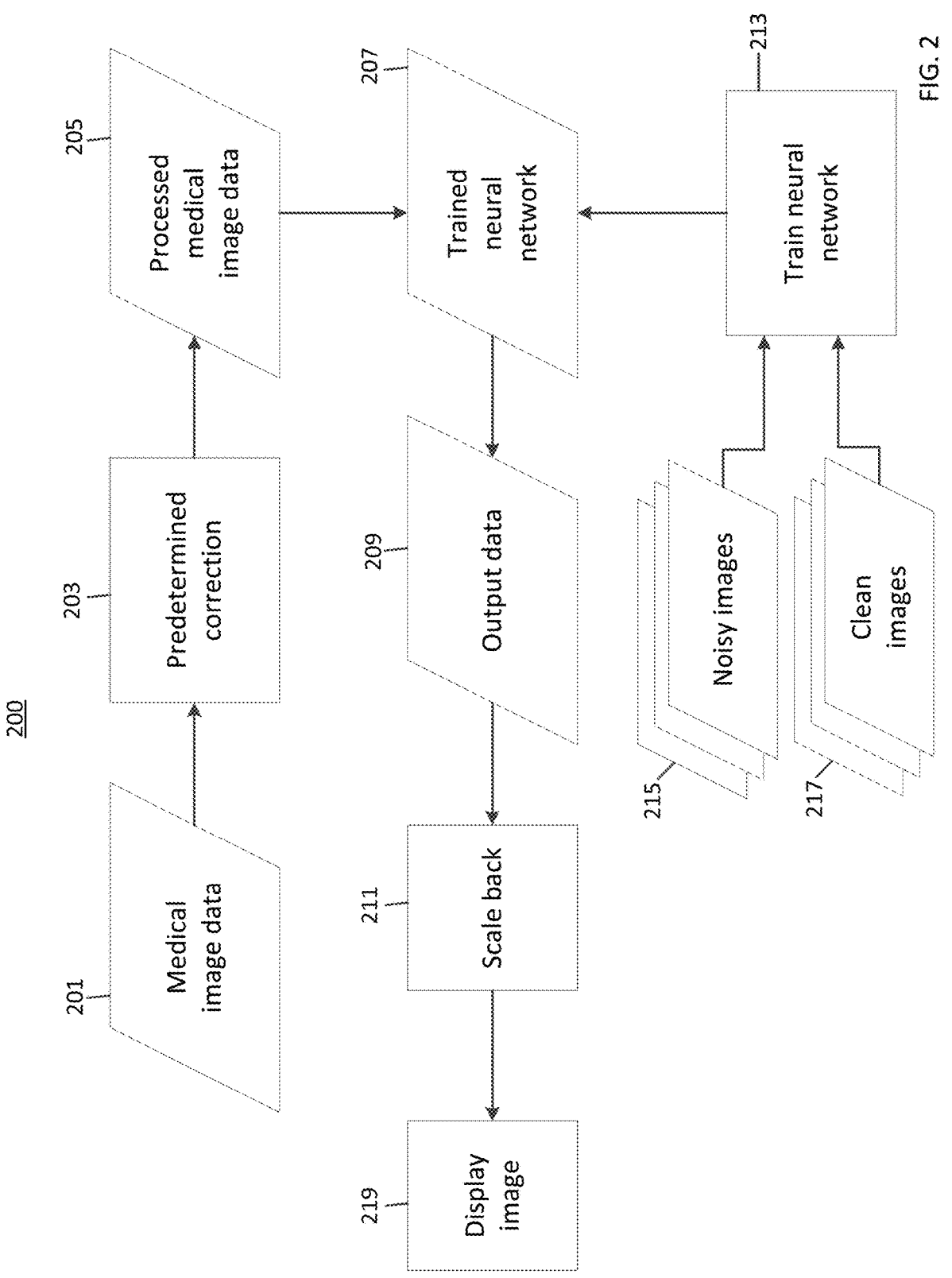
FIG. 2 illustrates a workflow for a method of utilizing a neural network trained with data having a first noise characteristic by performing a predetermined correction on noise characteristic information of to-be-processed medical image data to resemble the first noise characteristic.

As previously discussed, the noise characteristic information can be utilized in various ways. FIG. 2 shows a method 200 according to one embodiment of the present disclosure, where a neural network is utilized.

First, a neural network, such as a deep convolutional neural network, can be trained. The training data can include noisy images 215 and their corresponding clean images 217, where the noisy images 215 and clean images 217 all have the same noise characteristic information. Each noisy image in the set of noisy images 215 and their corresponding clean image in the set of clean images 217 are used as training pairs in step 213. The noisy images 215 can be used as input learning data, and the clean images 217 can be used at target learning data. Training a neural network in step 213 can be performed until a predetermined stopping criteria has been met (e.g. validation error is minimum). Upon completion of step 213, a trained neural network 207 is generated.

Different neural network structures, such as multilayer perceptron or U-net, can be implemented during training in step 213. In one embodiment, if the whole network is treated as a function $f$, the framework (parameter set $\Theta$) can be trained to minimize the loss function L as follow:

$$\hat{\Theta} = \arg\ \min_{\Theta} L(f_{\Theta}(X_{High}), X_{Low})$$

where $X_{Low}$ is a clean image, $X_{High}$ is a noisy image.

The noisy images 215 and clean images 217 can be acquired in a variety of ways, as can be appreciated by one of skill in the art. For example, clean images 217 can be obtained first (e.g., via simulation, real scan of object), and noise can be added to the clean images 217 for generating noisy images 215. As another example, noisy images 215 can be obtained first (e.g. via simulation, real scan of object), and the noisy images 215 can be denoised using any technique known by one of skill in the art for generating clean images 217.

Now that neural network training is complete, obtain medical image data 201. The medical image data 201 includes IQ signal data from a scan. Each data point in the IQ signal data is a complex number. This to-be-processed medical image data 201 can be acquired from a patient scan, such as a scan in a Doppler ultrasound or B-mode ultrasound. The accompanying noise characteristic information for the medical image data can be made known using either of the previously mentioned techniques (e.g. analyzing system parameters of the system that obtained the medical image data, performing a pre-scanning scheme using the system that obtained the medical image data). Note the noise characteristic information of the medical image data 201 can be different than the noise characteristic information of the noisy images 215 and clean images 217.

The next step 203 is performing predetermined correction. Essentially, the noise characteristic information of the medical image data 201 is normalized to resemble the noise characteristic information of the noisy images 215 and clean images 217 used as training data to train the trained neural network 207. Normalization can be across the entire depth of a scan, or across a specific range of depths. In one embodiment, normalizing can include determining a ratio between (1) the noise characteristic information of the medical image data 201 at a depth value and (2) the noise characteristic information of the noisy images 215/clean images 217 at the same depth value, where the medical image data 201 at the same depth value is then scaled according to the ratio. For example, if the noise characteristic information of the medical image data 201 is represented by $\sigma_{to\_be\_processed}$ at a specific depth and the noise characteristic information of the noisy images 215 and clean images 217 is represented by a $\sigma_{reference}$ at the same depth, normalizing can be multiplying pixel values of the medical image data 201 at the same depth by $$\frac{\sigma_{reference}}{\sigma_{to\_be\_processed}}.$$

Noise characteristic information of the noisy images 215 and clean images 217 can be obtained before performing the normalizing using any of the previously mentioned techniques (e.g. analyzing system parameters of system used to obtain training data, pre-scanning scheme in system used to obtain training data). This normalization process can be repeated across the entire depth of an object, or across a specific range of depths.

To provide a simple example to illustrate one embodiment for normalizing, if $$\frac{\sigma_{reference}}{\sigma_{to\_be\_processed}} = 0.5$$

6 at depth x, where x is a physical depth (e.g., 5 cm), and the I values of the medical image data 201 at depth x are each represented by [20, 23, 27, 40, 28], normalizing can update the I values of medical image data 201 at depth x to be [10, 11.5, 13.5, 20, 14]. Then if $$\frac{\sigma_{reference}}{\sigma_{to\_be\_processed}} = 0.3$$

at depth x+1, where the pixels at depth x+1 are located directly underneath the pixels at depth x, and the I values of the medical image data 201 at depth x−1 are represented by [33, 39, 42, 45, 36], normalizing can update the I values of medical image data 201 at depth x+1 to be [11, 13, 14, 15, 12]. Such a process can be repeated for every depth of interest (e.g., x+2, x+3, x+4, etc.) for the remaining I values in the data. The process would then be repeated for all the corresponding Q values of the medical data noting that the I values and the Q values share the same noise curve.

Upon completion of step 203, processed medical image data 205 is generated. The processed medical image data 205 is based on the medical image data from step 201, but now has altered noise characteristic information, resembling the noise characteristic information of the noisy images 215 and clean images 217.

Figure 3A:
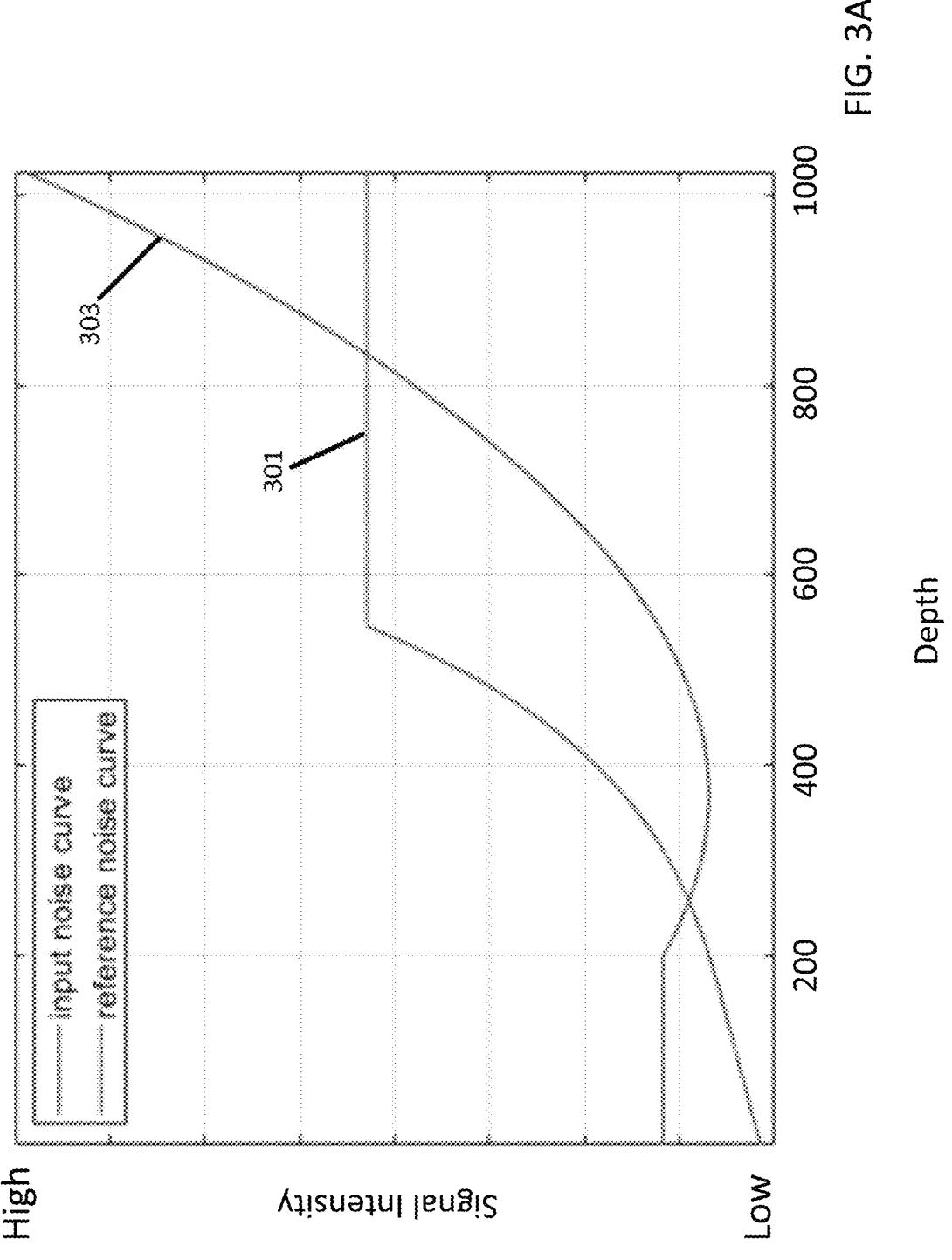
FIG. 3A illustrates a reference noise curve used in training a neural network, and an input noise curve from to-be-processed medical image data, according to one embodiment of the present disclosure.

Additional discussion related to method 200 will briefly be discussed with reference to FIG. 3A. FIG. 3A shows a reference noise curve 301 and input noise curve 303. The reference noise curve 301 (i.e., reference noise characteristic information) is the noise characteristic information of the training data (e.g., noisy images 215 and clean images 217) used for training a neural network (e.g. trained neural network 207). Note that the reference noise curve 301 levels off around depth 550 because of saturation. The input noise curve 303 is noise characteristic information of medical image data that is to-be-processed (e.g., medical image data 201). The predetermined correction performed in step 203 in method 200 normalizes the input noise curve 303, obtained from a particular scan configuration, to resemble the reference noise curve 301, obtained from a different scan configuration.

In FIG. 3A. the depth has 1024 samples corresponding to 20 centimeters. Of course, in other embodiments, a different sampling rates and/or different amounts of samples may be used. For example, 2048 samples can be used for a physical depth of 30 cm.

Returning back to FIG. 2, the processed medical image data 205 is input into the trained neural network 207, where the trained neural network 207 generates output data 209. The output data 209 has denoised IQ signal data, and now represent a medical image that is cleaner than a medical image that would be produced using the processed medical image data 205.

In step 211, output data 209 is scaled by a reciprocal of the ratio used to perform the predetermined correction in step 203. For example, since the medical image data 201 was normalized using $$\frac{\sigma_{reference}}{\sigma_{to\_be\_processed}}$$

in step 203, scaling back in step 211 can look like multiplying output data 209 by $$\frac{\sigma_{to\_be\_processed}}{\sigma_{reference}}.$$

Finally, step 211 is to transform the output data 209, now with denoised IQ signal data, into an image for displaying via a display unit.

Figure 3B:
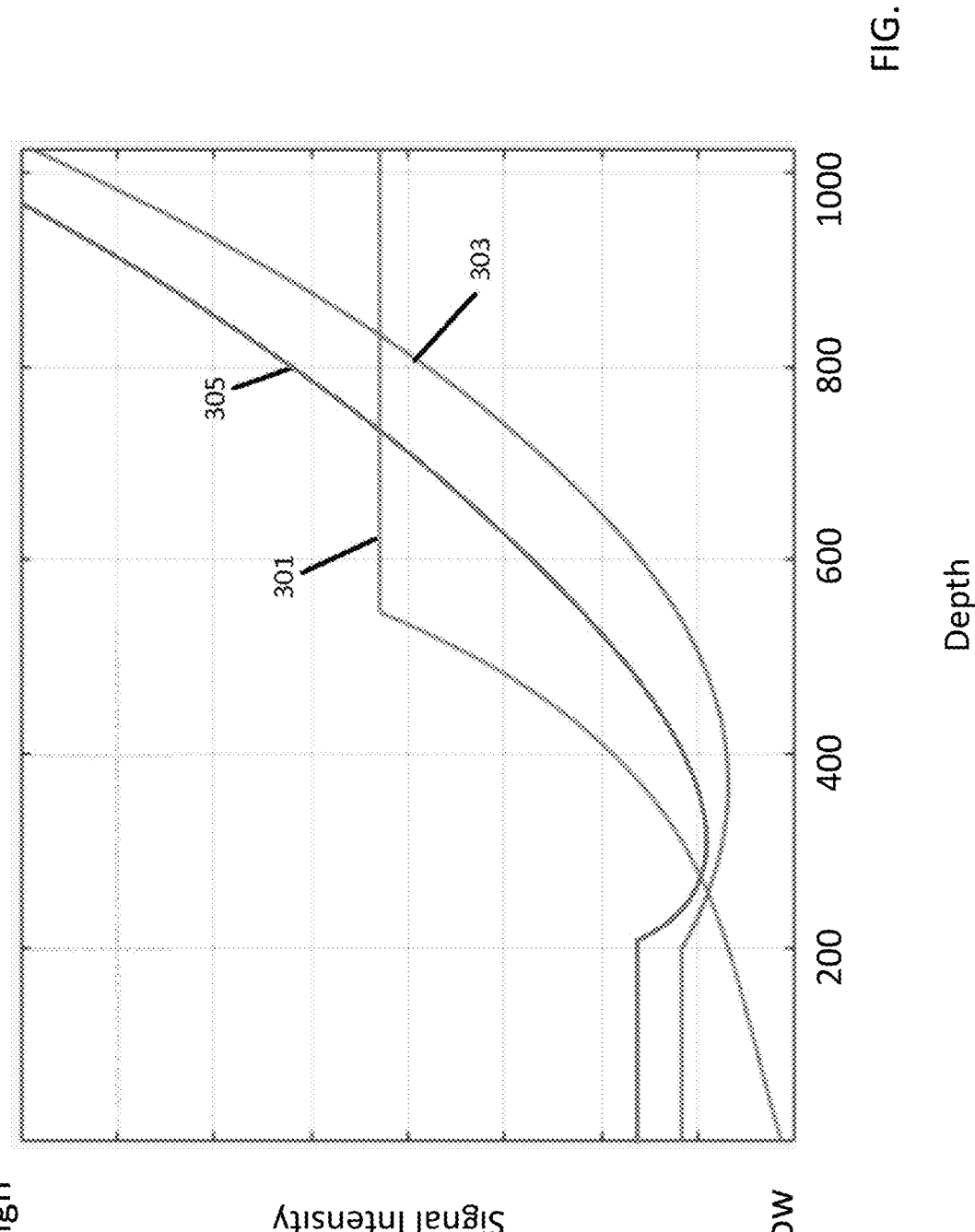
FIG. 3B illustrates two reference noise curves used in training two neural networks, and an input noise curve from to-be-processed medical image data, according to one embodiment of the present disclosure

Another embodiment will be discussed with reference to FIG. 3B. FIG. 3B is nearly identical to FIG. 3A, except there is an additional reference noise curve 305. In one embodiment, a first neural network can be trained using noisy/clean pairs having noise characteristic information as represented by reference noise curve 301, and a second neural network can be trained using noisy/clean pairs having noise characteristic information as shown by reference noise curve 305. Thereafter, either the first or second neural network can be chosen depending on the input noise curve 303. In one embodiment, the second neural network can chosen because reference noise curve 305 more closely resembles input noise curve 303. Thereafter, the input noise curve 303 can be normalized to resemble reference noise curve 305 in step 203 of method 200. In one embodiment, the reference noise curves can be obtained using system parameters of a system that will perform the imaging, or a pre-scanning of air by the system. Additional details regarding training neural networks with training pairs having different noise characteristic information will be discussed later with reference to FIG. 4.

Figure 4:
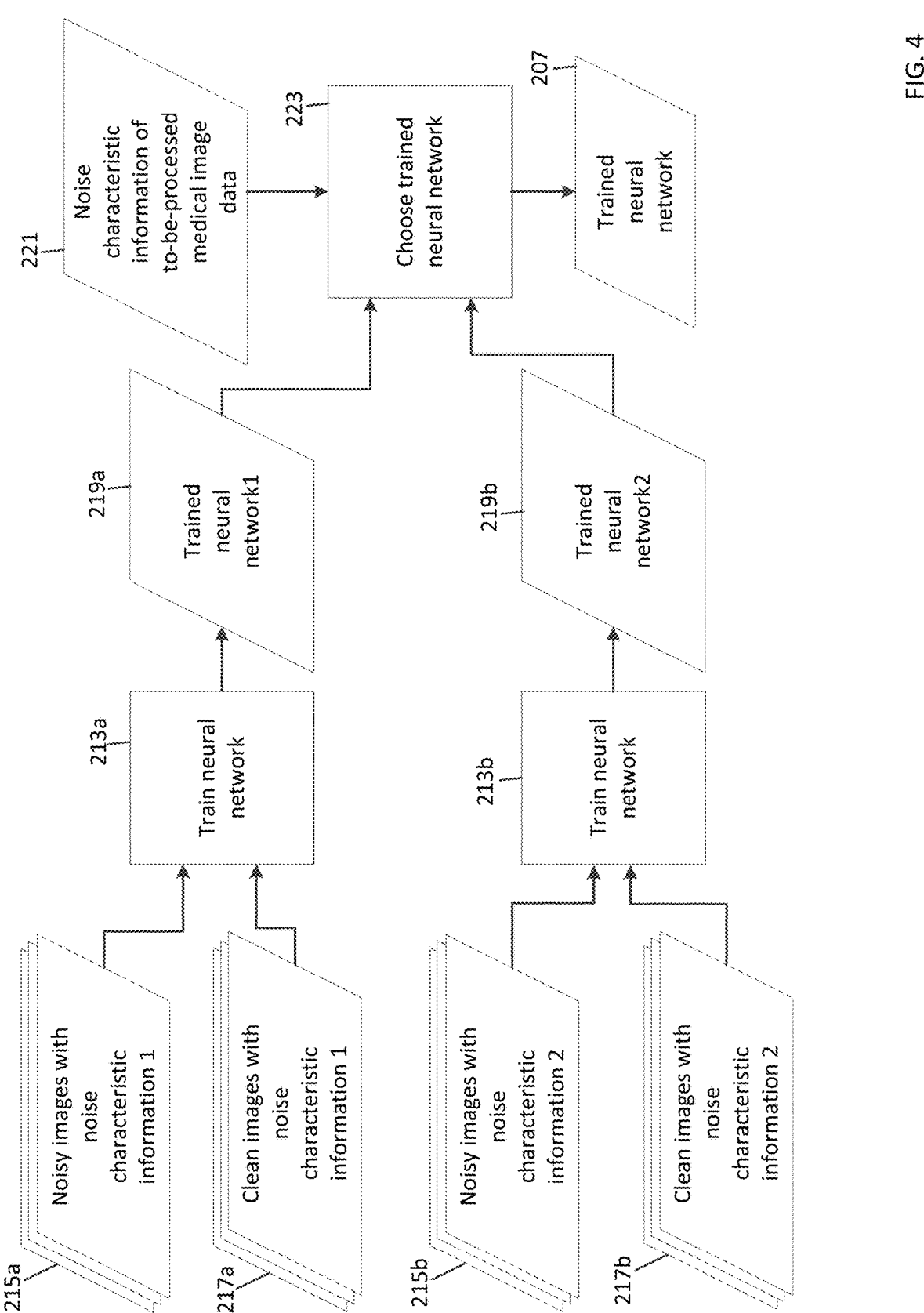
FIG. 4 illustrates another method for generating a trained neural network, where the trained neural network is chosen from one or more neural networks each trained using training dataset with unique noise characteristic information, according to one embodiment of the present disclosure.

FIG. 4 shows a method of another embodiment for generating the trained neural network 207 used in method 200. Rather than obtaining noisy images 215 and clean images 217 with one type of noise characteristic information for training a neural network, multiple sets of noisy/clean image pairs with different noise characteristic information can be used to train multiple neural networks. From there, the most suitable trained neural network can be used for processing to-be-processed data.

Noisy images with noise characteristic 1 215a and corresponding clean images with noise characteristic information 1 217a can be used in step 213a to produce trained neural network 1 219a. Noisy images with noise characteristic information 1 215a and clean images with noise characteristic information 1 217a have the same noise characteristic information. In step 213a, each noisy image is used as input learning data, and its corresponding clean image is used as output learning data. The result is a trained neural network, where the trained neural network used training data with the same noise characteristic information.

Likewise, noisy images with noise characteristic 2 215b and corresponding clean images with noise characteristic information 2 217b can be used in step 213b to produce trained neural network 2 219b in step 213b. Noisy images with noise characteristic information 2 215b and clean images with noise characteristic information 2 217b have the same noise characteristic information as each other, but different noise characteristic information than noisy images with noise characteristic 1 215a and clean images with noise characteristic information 1 217a. Note that the same loss function shown in equation 1 above can be used in steps 213a and 213b.

The result is trained neural network 1 219a trained with training data having a first type of noise characteristic, and trained neural network 2 219b trained with training data having a second type of noise characteristic. Of course, it can be appreciated that more than two trained neural networks can be produced using training data having additional noise characteristics in other embodiments.

Next, noise characteristic information of to-be-processed medical image data 221 is obtained. This is the noise characteristic information of the medical image data 201 from method 200.

In step 223, the noise characteristic information of to-be-processed medical image data 221 is used to determine whether to use trained neural network 1 219a or trained neutral network 2 219b. In one embodiment, the neural network trained using training data with noise characteristic information most similar to the noise characteristic information of to-be-processed medical image data 221 is chosen. The chosen neural network from step 223 is then used as the trained neural network 207 in method 200.

Thus far, the discussions presented herein were in 1D and assumed that the depth direction and the beam direction were the same. In one embodiment, noise characteristic information for the noisy/clean image pairs used to train the chosen neural network can be extended in the beam direction (in 2D) and used as an additional channel input into the trained neural network 207. Extending in the beam direction can mean that normalizing is done in both the depth direction and beam direction even if their directions are not the same.

As previously mentioned, the noise characteristic information can be utilized in various ways. In another embodiment, the noise characteristic information can be used directly in training. In this case, a trained deep convolutional neural network can directly handle medical image data with various noise characteristics.

Figure 5:
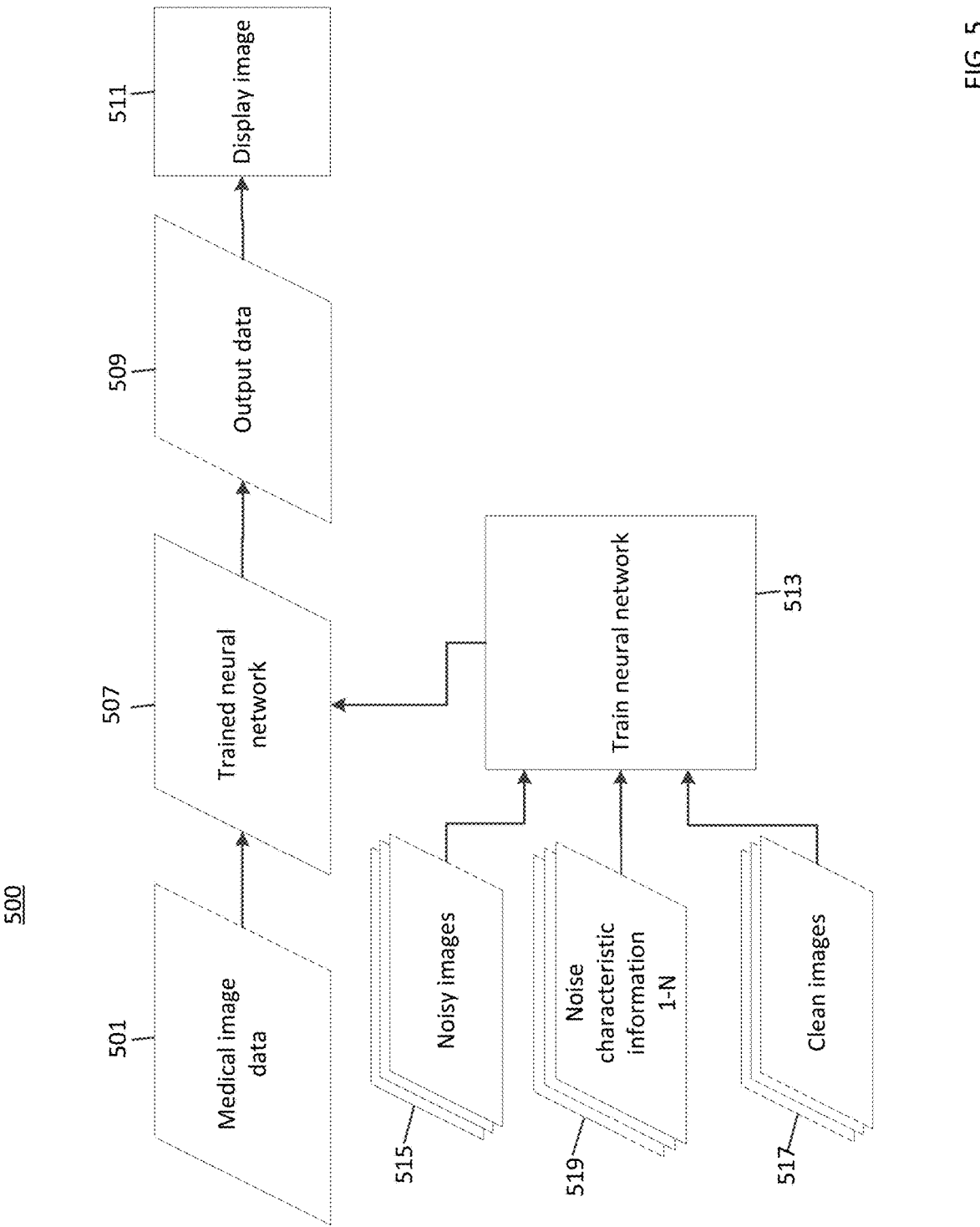
FIG. 5 illustrates a workflow for a method of generating and using a trained neural network capable of handling medical image data with various noise characteristics, according to one embodiment of the present disclosure.

FIG. 5 is a workflow illustrating another method 500 according to one embodiment of the present disclosure. Method 500 utilizes various noise characteristic information directly in training, allowing the trained neural network to handle to-be-processed medical image data with varying noise characteristic information.

Step 513 is training a neural network to produce a trained neural network 507. The training data for training a neural network in step 513 includes noisy images 515, their corresponding clean images 517, and their corresponding noise characteristic information 1-N 519. N can be one or more, and indicates that noise characteristic information for corresponding noisy and clean images can vary during training. Noisy images 515 and noise characteristic information 1-N 519 are used as input learning data, and the clean images 517 are used as output learning data. If the whole network is treated as a function $f$, the framework (parameter set $\Theta$) can be trained to minimize the loss function L as follow:

$$\hat{\Theta} = \arg \min_{\Theta} L(f_\Theta(X_{High}), X_{Low})$$

where $k_{Low}$ is a clean image, $X_{High}$ is a noisy image, and noise is the noise characteristic information of $X_{Low}$ and $X_{High}$.

As previously discussed, the noisy images 515 and clean images 517 can be obtained using any technique known by one of skill in the art (e.g. denoising noisy images 515, corrupting clean images 517). Additionally, the noisy characteristic information 1-N 519 can be obtained using any technique known by one of skill in the art (e.g. system parameters, pre-scanning scheme).

Now that neural network training is complete, medical image data 501 and its corresponding noise characteristic information is acquired. This to-be-processed medical image data 501 can be acquired from a patient scan, such as a scan in a Doppler ultrasound or B mode ultrasound. The noise characteristic information for the medical image data 501 can be acquired using any of the previously mentioned techniques (e.g. system parameters, pre-scanning scheme). The obtained medical image data 501 and its corresponding noise characteristic information is input into the trained neural network 507, thereby generating output data 509. The output data 509 has IQ signal data that is less noisy than that of the medical image data 501. The output data 509 is then transformed into an image and used in step 511 to display the image via a display unit.

Figure 6:
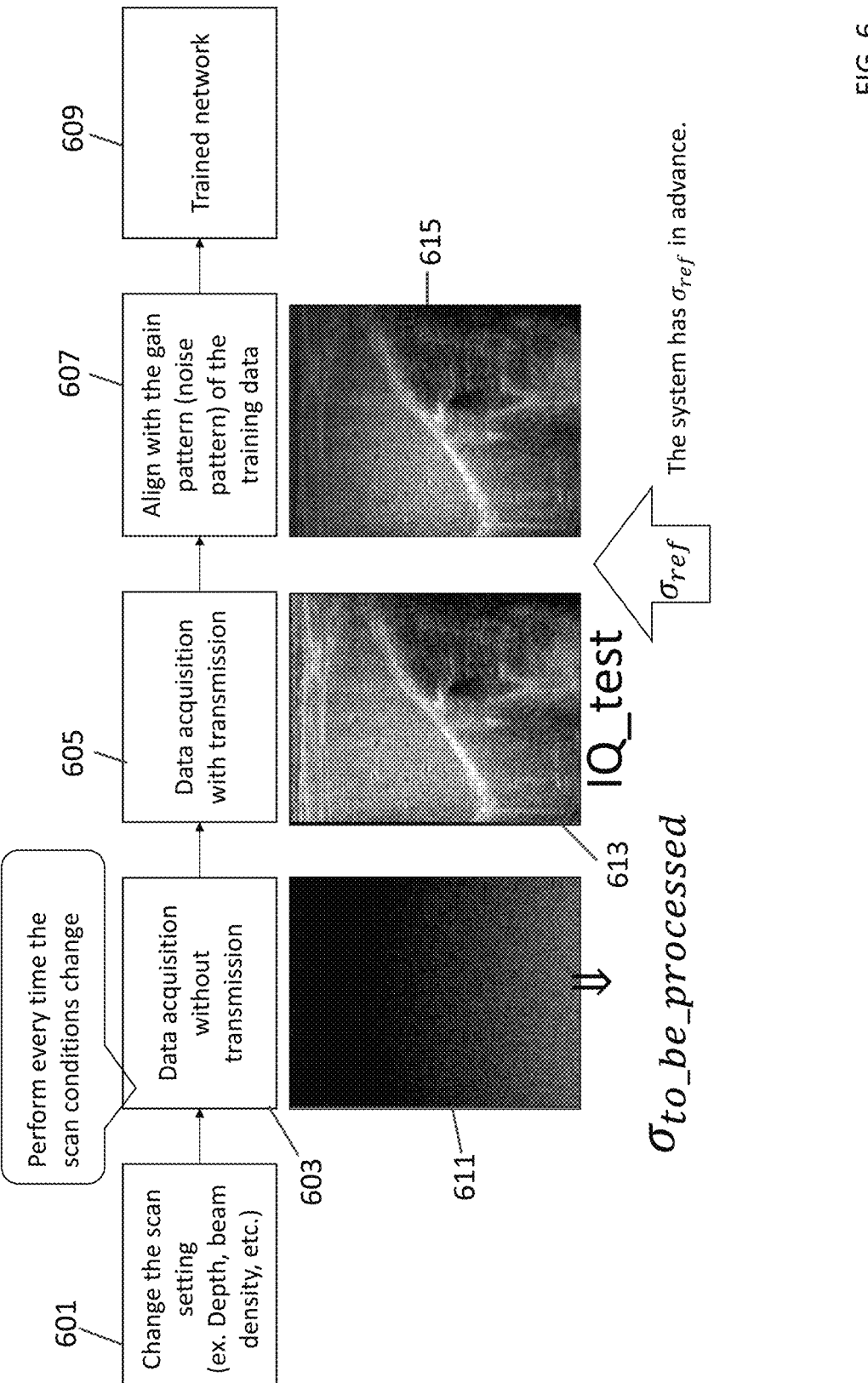
FIG. 6 is a workflow illustrating performing a data acquisition without and with transmission and aligning the data acquisition with transmission to have the reference noise characteristic information of the training data, according to one embodiment of the present disclosure.

FIG. 6 illustrates a workflow diagram with exemplary illustrations, according to one exemplary embodiment of the present disclosure. In step 601, scan settings for an ultrasound scan are changed to have a desired configuration (e.g. depth, beam density), and the process discussed below is run again each time that the scan setting are changed. Alternatively, the process can be run again when a set of scan conditions has not been used for some predetermined period of time (e.g., 24 hours, 1 week, or 1 month). This avoids the need to re-calibrate every time the scan conditions are changed. The ultrasound device may prompt the healthcare provider to run the calibration when needed.

Next, in step 603, a data acquisition without transmission (i.e., a pre-scanning method) is performed. This can look like performing two consecutive air scans in the same ultrasound scanner and subtracting the consecutive air scan data from each other. Image 611 is an example of a data acquisition without transmission. In image 611, each horizontal line of pixels is noise at a specific depth, represented by $\sigma_{to\_be\_processed}$, where the lower a horizontal line of pixels is located in image 611, the larger the depth value (i.e., deeper in an object). Of course, the value of $\sigma_{to\_be\_processed}$ typically changes depending on the corresponding depth, as shown in image 611. Image 611 and input noise curve 303 can be thought of as different ways to represent the same noise information.

In step 605, a data acquisition with transmission is performed in the same ultrasound scanner. An example output from step 605 is represented by image 613. IQ_test represents pixel values across a horizontal line for image 613 at the same depth as that represented by $\sigma_{to\_be\_processed}$.

In step 607, the data acquisition with transmission from step 605 is aligned with the gain pattern (i.e. noise pattern, noise characteristic information) of the training data. The gain pattern of the training data is represented by $\sigma_{ref}$ (for the same depth as IQ_test and $\sigma_{to\_be\_processed}$). The same techniques discussed above regarding normalizing can be applied here. IQ_test can be multiplied by $$\frac{\sigma_{ref}}{\sigma_{to\_be\_processed}}\left(\text{or }\frac{\sigma_{to\_be\_processed}}{\sigma_{ref}}\right)$$

to normalize the noise characteristic information of image 613 to resemble that of training data for a specific depth; this process can be repeated for each depth of interest. Image 615 is an example of an image whose noise characteristic information has been normalized across the entire depth. Lastly, the output of step 607 is input into a trained network in step 609 for denoising the IQ signal data.

The techniques discussed in the present disclose use trained models, such as a neural network, to perform denoising of images, such as B-mode or Doppler ultrasound images. With understanding of noise characteristic information from one or more varying data acquisition modes (i.e. scan conditions), a trained model can be introduced to denoise collected image data. Under such a framework, better signal to noise ratio can be achieved. Furthermore, it can lead to low acoustic power ultrasound imaging, which reduces patient dose.

The techniques discussed herein utilize different noise information under different data acquisition modes. With proposed framework, the trained model is robust and can be applied to different scan conditions.

In one embodiment, it can be appreciated that the above mentioned techniques can be viewed in a system, such as an ultrasound diagnosis apparatus.

Figure 7:
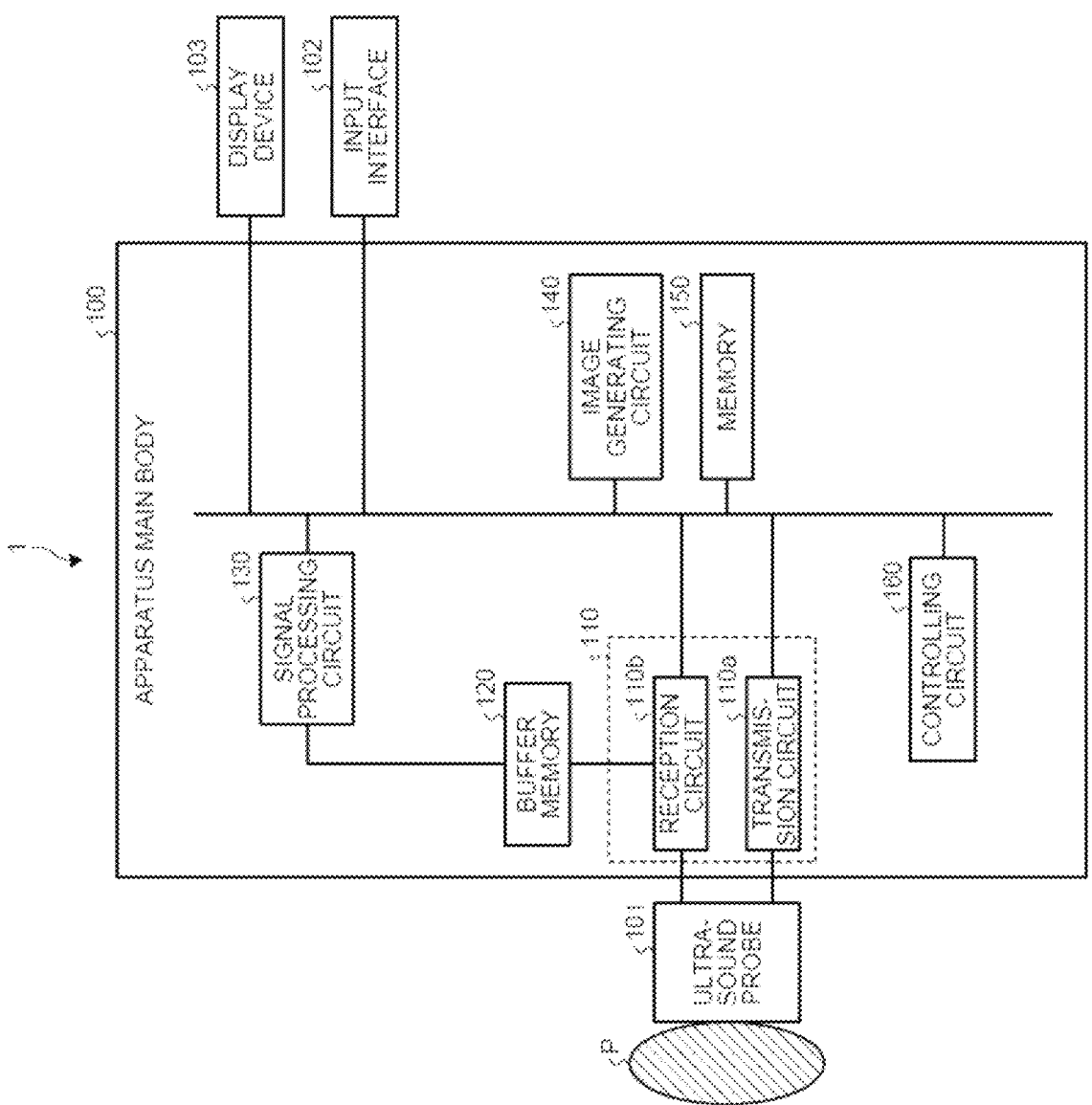
FIG. 7 is a block diagram of an ultrasound system, according to one embodiment of the present disclosure.

FIG. 7 is a block diagram illustrating an exemplary configuration of an ultrasound diagnosis apparatus 1 according to a first embodiment. As illustrated in FIG. 7, the ultrasound diagnosis apparatus 1 according to the first embodiment includes an apparatus main body 100, an ultrasound probe 101, an input interface 102, and a display unit 103.

For example, the ultrasound probe 101 includes a plurality of transducer elements such as piezoelectric transducer elements. Each of the plurality of transducer elements is configured to generate an ultrasound wave on the basis of a drive signal supplied thereto from a transmission circuit 110a of a transmission and reception circuit 110 included in the apparatus main body 100. Further, the ultrasound probe 101 is configured to receive reflected waves from an examined subject (hereinafter "patient") P, to convert the received reflected waves into reflected-wave signals each being an electrical signal, and to output the reflected-wave signals to the apparatus main body 100. Further, for example, the ultrasound probe 101 includes a matching layer provided for the transducer elements, a backing member that prevents the ultrasound waves from propagating rearward from the transducer elements, and the like. The ultrasound probe 101 is detachably connected to the apparatus main body 100.

When an ultrasound wave is transmitted from the ultrasound probe 101 to the patient P, the transmitted ultrasound wave is repeatedly reflected on a surface of discontinuity of acoustic impedances at a tissue in the body of the patient P and is received as a reflected wave by the plurality of transducer elements included in the ultrasound probe 101. The amplitude of the received reflected wave is dependent on the difference between the acoustic impedances on the surface of discontinuity on which the ultrasound wave is reflected. When a transmitted ultrasound pulse is reflected on the surface of a moving blood flow, a cardiac wall, or the like, the reflected wave is, due to the Doppler effect, subject to a frequency shift, depending on a velocity component of the moving members with respect to the ultrasound wave transmission direction. Further, the ultrasound probe 101 is configured to output the reflected-wave signals to a reception circuit 110b of the transmission and reception circuit 110 (explained later).

The ultrasound probe 101 is provided so as to he attachable to and detachable from the apparatus main body 100. When a two-dimensional region in the patient P is to be scanned (a two-dimensional scan), the user connects, for example, a one-dimensional (1D) array probe in which the plurality of transducer elements are arranged in a row to the apparatus main body 100 as the ultrasound probe 101. Possible types of the 1D array probe include a linear ultrasound probe, a convex ultrasound probe, and a sector ultrasound probe. In contrast, when a three-dimensional region in the patient P is to be scanned (a three-dimensional scan), the user connects, for example, a mechanical four-dimensional (4D) probe or a two-dimensional (2D) array probe to the apparatus main body 100 as the ultrasound probe 101. The mechanical 4D probe is capable of performing a two-dimensional scan by using the plurality of transducer elements arranged in a row similarly to those in the 1D array probe and is also capable of performing a three-dimensional scan by swinging the plurality of transducer elements at a predetermined angle (a swinging angle). Further, the 2D array probe is capable of performing a three-dimensional scan by using the plurality of transducer elements arranged in a matrix formation and is capable of performing a two-dimensional scan by converging and transmitting ultrasound waves.

The input interface 102 is realized by input means such as, for example, a mouse, a keyboard, a button, a panel switch, a touch command screen, a foot switch, a trackball, a joystick, and/or the like. The input interface 102 is configured to receive various types of setting requests from a user of the ultrasound diagnosis apparatus 1 and to transfer the received various types of setting requests to the apparatus main body 100.

The display unit 103 is configured, for example, to display a Graphical User Interface (GUI) used by the user of the ultrasound diagnosis apparatus 1 for inputting the various types of setting requests through the input interface 102 and to display an ultrasound image based on ultrasound image data generated by the apparatus main body 100 and the like. The display unit 103 is realized by using a liquid crystal monitor, a Cathode Ray Tube (CRT) monitor, or the like.

The apparatus main body 100 is configured to generate the ultrasound image data on the basis of the reflected-wave signals transmitted thereto from the ultrasound probe 101. The ultrasound image data is an example of image data. The apparatus main body 100 is capable of generating two-dimensional ultrasound image data on the basis of reflected-wave signals corresponding to a two-dimensional region of the patient P and being transmitted thereto from the ultrasound probe 101. Further, the apparatus main body 100 is also capable of generating three-dimensional ultrasound image data on the basis of reflected-wave signals corresponding to a three-dimensional region of the patient P and being transmitted thereto from the ultrasound probe 101. As illustrated in FIG. 7, the apparatus main body 100 includes the transmission and reception circuit 110, a buffer memory 120, a signal processing circuit (signal processing circuitry) 130, an image generating circuit (image generating circuitry) 140, a memory 150, and a controlling circuit (controlling circuitry) 160.

Under control of the controlling circuit 160, the transmission and reception circuit 110 is configured to cause the ultrasound waves to be transmitted from the ultrasound probe 101 and to cause the ultrasound waves (the reflected waves of the ultrasound waves) to be received by the ultrasound probe 101. In other words, the transmission and reception circuit 110 is configured to perform a scan via the ultrasound probe 101. The scanning may be referred to as a scan, an ultrasound scan, or ultrasound scanning. The transmission and reception circuit 110 is an example of a transmitting and receiving unit. The transmission and reception circuit 110 includes the transmission circuit 110a and the reception circuit 110b.

Under the control of the controlling circuit 160, the transmission circuit 110a is configured to cause the ultrasound waves to be transmitted from the ultrasound probe 101. The transmission circuit 110a is configured to supply the drive signal (a transmission pulse of the drive signal) to the ultrasound probe 101. When a two-dimensional region in the patient P is to be scanned, the transmission circuit 110a is configured to cause an ultrasound beam for scanning the two-dimensional region to be transmitted from the ultrasound probe 101. In another example, when a three-dimensional region in the patient P is to be scanned, the transmission circuit 110a is configured to cause an ultrasound beam for scanning the three-dimensional region to be transmitted from the ultrasound probe 101. The transmission circuit 110a will be explained later.

The transmission circuit 110a has a function of performing a prescribed delay process on the drive signal and supplying the drive signal on which the prescribed delay process has been performed to the transducer elements. In the present embodiment, for example, one channel is assigned to each of the transducer elements, so that the prescribed delay process is performed on the drive signal with respect to each of the channels. As a result, the transmission circuit 110a is configured, for example, to control transmission directionality of the ultrasound waves by converging the ultrasound waves emitted from the transducer elements into a beam form.

The reflected waves of the ultrasound waves transmitted by the ultrasound probe 101 reach the transducer elements provided inside the ultrasound probe 101 and are subsequently converted from mechanical vibration into the electrical signals (the reflected-wave signals) at the transducer elements, before being input to the reception circuit 110b. The reception circuit 110b includes a pre-amplifier, an Analog-to-Digital (A/D) converter, a reception delay circuit, an adder, and the like and is configured to generate reflected-wave data by performing various types of processes on the reflected-wave signals transmitted thereto from the ultrasound probe 101. After that, the reception circuit 110b is configured to store the generated reflected-wave data into the buffer memory 120.

The pre-amplifier is configured to make a gain adjustment (a gain correction) by amplifying the reflected-wave signal with respect to each of the channels. The A/D converter is configured to convert the gain-corrected reflected-wave signals into digital signals, by performing an A/D conversion on the gain-corrected reflected-wave signals. The reception delay circuit is configured to apply a delay time period necessary for determining reception directionality, to the reflected-wave signals that were converted into the digital signal.

The adder is configured to generate the reflected-wave data (a Radio Frequency [RF] signal) by performing an adding process on the reflected-wave signals processed by the reception delay circuit. After that the adder is configured to store the reflected-wave data into the buffer memory 120. As described herein, in the present embodiment, the reception delay circuit and the adder perform a phased addition process. In the present embodiment, for example, one channel is assigned to each of the transducer elements. Further, the reception delay circuit is configured to apply the delay time period to the reflected-wave signal of each of the channels, whereas the adder is configured to perform the adding process of adding together the plurality of reflected-wave signals to which the delay time periods were applied by the reception delay circuit.

The reception circuit 110b is configured to generate two-dimensional reflected-wave data from the two-dimensional reflected-wave signals transmitted thereto from the ultrasound probe 101. In another example, the reception circuit 110b is configured to generate three-dimensional reflected-wave data from the three-dimensional reflected-wave signals transmitted thereto from the ultrasound probe 101.

The buffer memory 120 is a memory configured to temporarily store therein the reflected-wave data generated by the transmission and reception circuit 110. For example, under control of the reception circuit 110*b,* the buffer memory 120 is configured to be able to store therein a prescribed number of pieces of reflected-wave data each corresponding to one frame. Further, while having stored therein the prescribed number of pieces of reflected-wave data each corresponding to one frame, when another piece of reflected-wave data corresponding to one frame is newly generated by the reception circuit 110*b,* the buffer memory 120 is configured, under the control of the reception circuit 110*b,* to discard a piece of reflected-wave data corresponding to one frame that was generated earliest and to store therein the newly-generated piece of reflected-wave data corresponding to the one frame. For example, the buffer memory 120 is realized by using a semiconductor memory element such as a Random Access Memory (RAM) or a flash memory.

The signal processing circuit 130 is configured to read the reflected-wave data from the buffer memory 120, to perform various types of signal processing processes on the read reflected-wave data, and to output the reflected-wave data on which the various types of signal processing processes have been performed to the image generating circuit 140 as B-mode data or Doppler data. The signal processing circuit 130 is realized by using a processor, for example. The signal processing circuit 130 is an example of a signal processing unit.

For example, the signal processing circuit 130 is configured to generate B-mode data in which the signal intensity (amplitude intensity) at each sampling point is expressed by a degree of brightness. by performing an orthogonal detection as well as a logarithmic amplification, an envelope detecting process, and/or the like on the reflected-wave data read from the buffer memory 120. For example, the signal processing circuit 130 is configured to output the generated B-mode data to the image generating circuit 140.

Further, the signal processing circuit 130 is configured to perform a signal processing process to realize harmonic imaging by which a higher harmonic component is visualized in an image. Examples of the harmonic imaging include Contrast Harmonic Imaging (CHI) and Tissue Harmonic Imaging (THI). Further, for the contrast harmonic imaging and the tissue harmonic imaging, the following scan methods are known, for example: Amplitude Modulation (AM) methods, Phase Modulation (PM) methods called a pulse subtraction method and a pulse inversion method, and AMPM methods in which advantageous effects of both the AM and the PM methods arc achieved by combining the AM and the PM methods together.

The signal processing circuit 130 is configured to extract movement information of moving members (a blood flow, a tissue, a contrast agent echo component, and/or the like) based on the Doppler effect from the reflected-wave data, by performing a frequency analysis on the reflected-wave data read from the buffer memory 120 and to generate Doppler data indicating the extracted movement information. For example, the signal processing circuit 130 is configured to generate the Doppler data indicating the extracted movement information of the moving members, by extracting, as the movement information of the moving members, an average velocity value, an average dispersion value, an average power value, and the like with respect to multiple points. The signal processing circuit 130 is configured to output the generated Doppler data to the image generating circuit 140.

By using the functions of the signal processing circuit 130 described above, the ultrasound diagnosis apparatus 1 according to an embodiment is capable of implementing a color Doppler method that may be called a Color Flow Mapping (CFM) method. According to the color flow mapping method, ultrasound wave transmission and reception is performed multiple times on a plurality of scanning lines. Further, according to the color flow mapping method, a signal (a blood flow signal) derived from a blood flow is extracted by applying a Moving Target Indicator (MTI) filter to data sequences in mutually the same position, while suppressing signals (clutter signals) derived from stationary tissues or a slow-moving tissues within the data sequences in mutually the same position. Further, according to the color flow mapping method, blood flow information such as velocity of the blood flow, dispersion of the blood flow, power of the blood flow, and the like are estimated on the basis of the blood flow signal. The signal processing circuit 130 is configured to output Doppler data indicating the blood flow information estimated by implementing the color flow mapping method, to the image generating circuit 140.

The signal processing circuit 130 is capable of processing both types of reflected-wave data, namely, the two-dimensional reflected-wave data and the three-dimensional reflected-wave data.

The signal processing circuit 130 can execute all or portions of method 200 and/or 500, as well as discussed variations.

The image generating circuit 140 is configured to generate ultrasound image data from the B-mode data and the Doppler data output from the signal processing circuit 130. For example, the image generating circuit 140 is configured to generate two-dimensional B-mode image data in which the intensities of the reflected waves are expressed with brightness levels, from two-dimensional B-mode data generated by the signal processing circuit 130. Further, the image generating circuit 140 is configured to generate two-dimensional Doppler image data in which the movement information or the blood flow information is visualized in an image, from two-dimensional Doppler data generated by the signal processing circuit 130. The two-dimensional Doppler image data is velocity image data, dispersion image data, power image data, or image data combining together these types of image data. The image generating circuit 140 is realized by using a processor.

In this situation, generally speaking, the image generating circuit 140 is configured to convert (by performing a scan convert process) a scanning line signal sequence from an ultrasound scan into a scanning line signal sequence in a video format used by, for example, television and to generate display-purpose ultrasound image data. For example, the image generating circuit 140 is configured to generate the display-purpose ultrasound image data by performing a coordinate transformation process compliant with the ultrasound scanning mode used by the ultrasound probe 101 on the data output from the signal processing circuit 130. Further, as various types of image processing processes besides the scan convert process, the image generating circuit 140 is configured to perform, for example, an image processing process (a smoothing process) to re-generate an average brightness value image, an image processing process (an edge enhancement process) that uses a differential filter inside an image, or the like, by using a plurality of image frames resulting from the scan convert process. Also, the image generating circuit 140 is configured to combine text information of various types of parameters, scale graduations, body marks, and the like with the ultrasound image data.

Further, the image generating circuit 140 is configured to generate three-dimensional B-mode image data by performing a coordinate transformation process on three-dimensional B-mode data generated by the signal processing circuit 130. Further, the image generating circuit 140 is configured to generate three-dimensional Doppler image data by performing a coordinate transformation process on three-dimensional Doppler data generated by the signal processing circuit 130. In other words, the image generating circuit 140 is configured to generate the "three-dimensional B-mode image data and three-dimensional Doppler image data" as "three-dimensional ultrasound image data (volume data)". Further, the image generating circuit 140 is configured to perform various types of rendering processes on the volume data, so as to generate various types of two-dimensional image data used for displaying the volume data on the display unit 103.

Examples of the rendering processes performed by the image generating circuit 140 include a process of generating Multi Planar Reconstruction (MPR) image data from the volume data by using a Multi Planar Reconstruction (MPR) method. Further, other examples of the rendering processes performed by the image generating circuit 140 include a Volume Rendering (VR) process by which two-dimensional image data reflecting three-dimensional information is generated. The image generating circuit 140 is an example of an image generating unit.

The B-mode data and the Doppler data are each ultrasound image data before the scan convert process. The data generated by the image generating circuit 140 is the display-purpose ultrasound image data after the scan convert process. The B-mode data and the Doppler data may be referred to as raw data.

The memory 150 is a memory configured to store therein various types of image data generated by the image generating circuit 140. Further, the memory 150 is also configured to store therein the data generated by the signal processing circuit 130. The user is able to invoke the B-mode data and the Doppler data stored in the memory 150 after a diagnosis process, for example. The invoked data serves as display-purpose ultrasound image data after being routed through the image generating circuit 140.

Further, the memory 150 is also configured to store therein control programs for performing the scan (the ultrasound wave transmission and reception), image processing processes, and display processes, as well as various types of data such as diagnosis information (e.g., patient IDs, medical doctors' observations, etc.), diagnosis protocols, and various types of body marks. For example, the memory 150 is realized by using a semiconductor memory element such as a RAM or a flash memory, a hard disk, or an optical disk.

The controlling circuit 160 is configured to control the entirety of the processes performed by the ultrasound diagnosis apparatus 1. More specifically, the controlling circuit 160 is configured to control processes performed by the transmission and reception circuit 110, the signal processing circuit 130, and the image generating circuit 140, on the basis of the various types of setting requests input from the user via the input interface 102 and the various types of control programs and various types of data read from the memory 150. Further, the controlling circuit 160 is configured to control the display unit 103 so as to display ultrasound images based on the display-purpose ultrasound image data stored in the memory 150. For example, the controlling circuit 160 is realized by using a processor. The ultrasound images are examples of images.

Further, the controlling circuit 160 is configured to control the ultrasound scan by controlling the ultrasound probe 101 via the transmission and reception circuit 110.

The method and system described herein can be implemented in a number of technologies but generally relate to processing circuitry for performing the techniques described herein. In one embodiment, the processing circuitry is implemented as one of or as a combination of: an application specific integrated circuit (ASIC), a field programmable gate array (FPGA), a generic array of logic (GAL), a programmable array of logic (PAL), circuitry for allowing one-time programmability of logic gates (e.g., using fuses) or reprogrammable logic gates. Furthermore, the processing circuitry can include a computer processor and having embedded and/or external non-volatile computer readable memory (e.g., RAM, SRAM, FRAM, PROM, EPROM, and/or EEPROM) that stores computer instructions (binary executable instructions and/or interpreted computer instructions) for controlling the computer processor to perform the processes described herein. The computer processor circuitry may implement a single processor or multiprocessors, each supporting a single thread or multiple threads and each having a single core or multiple cores. In an embodiment in which neural networks are used, the processing circuitry used to train the artificial neural network need not be the same as the processing circuitry used to implement the trained artificial neural network that performs the denoising described herein. For example, processor circuitry and memory may be used to produce a trained artificial neural network (e.g., as defined by its interconnections and weights), and an FPGA may be used to implement the trained artificial neural network. Moreover, the training and use of a trained artificial neural network may use a serial implementation or a parallel implementation for increased performance (e.g., by implementing the trained neural network on a parallel processor architecture such as a graphics processor architecture).

Embodiments of the present disclosure may also be set forth in the following parentheticals.

(1) A medical image processing apparatus comprising: memory storing one or more trained models for denoising medical image data; processing circuitry configured to (1) obtain processed medical image data by normalizing noise characteristic information of the medical image data to resemble noise characteristic information of training data used for training a corresponding trained model of the one or more trained models and (2) input the processed medical image data into the corresponding trained model to obtain output data; and a display control circuitry configured to cause a display unit to display a medical image based on the obtained output data.

(2) The apparatus of (1), wherein the one or more trained models for denoising medical image data stored in the memory comprises plural trained models, the processing circuitry further comprising processing circuitry configured to choose the corresponding trained model from the plural trained models using system parameters of a system used to collect the medical image data.

(3) The apparatus of any one of (1) to (2), wherein the one or more trained models for denoising medical image data stored in the memory comprises plural trained models, the processing circuitry further comprising processing circuitry configured to choose the corresponding trained model from the plural trained models using a pre-scanning by the apparatus of air.

(4) The apparatus of any one of (1) to (3), wherein the noise characteristic information is depth-specific noise information related to an ultrasound scanner.

(5) The apparatus of any one of (1) to (4), wherein the medical image processing apparatus is an ultrasound scanner.

(6) The apparatus of any one of (1) to (5), wherein the noise characteristic information is depth-specific noise information related to the ultrasound scanner.

(7) The apparatus of any one of (1) to (6), wherein the ultrasound scanner performs ultrasound B-mode imaging.

(8) The apparatus of any one of (1) to (7), wherein the ultrasound scanner performs Doppler ultrasound.

(9) A medical image processing apparatus comprising: a memory storing a trained model generated by a machine-learning process based on first medical image data, noise characteristic information of the first medical image data, and second medical image data based on the first medical image data, the second medical image data having less noise than the first medical image data; processing circuitry configured to input medical image data into the trained model to obtain output data; and a display control circuitry configured to cause a display unit to display a medical image based on the obtained output data.

(10) The apparatus of (9), wherein the first medical image data and the noise characteristic information of the first medical image data are used as input learning data, and the second medical image data is used as output learning data.

(11) The apparatus of any one of (9) to (10), wherein the noise characteristic information of the first medical image data is obtained by analyzing system parameters of a system used to collect the first medical image data.

(12) The apparatus of any one of (9) to (11), wherein the noise characteristic information of the first medical image data is obtained by performing a pre-scanning scheme in a system used to collect the first medical image data.

(13) The apparatus of any one of (9) to (12), wherein the processing circuitry is further configured to input noise characteristic information of the medical image data into the trained model.

(14) A method comprising: obtaining processed medical image data by normalizing noise characteristic information of medical image data to resemble noise characteristic information of training data used for training a corresponding trained model from one or more trained models; inputting the processed medical image data into the corresponding trained model to obtain output data; and displaying a medical image based on the obtained output data.

(15) The method of (14), further comprising choosing the corresponding trained model from the one or more trained models using system parameters of a system used to collect the medical image data, wherein the one or more trained models comprises plural trained models.

(16) The method of any one of (14) to (15), further comprising choosing the corresponding trained model from the one or more trained models using a pre-scanning by the apparatus of air, wherein the one or more trained models comprises plural trained models.

(17) The method of any one of (14) to (16), wherein noise characteristic information is depth-specific noise information related to an ultrasound scanner.

(18) The method of claim any one of (14) to (17), wherein the medical image data is obtained from an ultrasound scanner.

(19) The method of any one of (14) to (18), wherein the noise characteristic information is depth-specific noise information related to the ultrasound scanner.

(20) The method of any one of (14) to (19), wherein the ultrasound scanner performs at least one of Doppler ultrasound and ultrasound B-mode imaging.

(21) The apparatus of any one of (1) to (13), wherein the medical image data is IQ data.

(22) The apparatus of any one of (1) to (13), wherein the medical image data is image data.

(23) The apparatus of any one of (1) to (13), wherein the medical image data is raw image data.

(24) The apparatus of any one of (1) to (13), wherein the medical image data is reconstructed image data.

(25) The apparatus of any one of (1) to (13), wherein the medical image data is RF data.

(26) The method of any one of (14) to (20), wherein the medical image data is IQ data.

(27) The method of any one of (14) to (20), wherein the medical image data is image data.

(28) The method of any one of (14) to (20), wherein the medical image data is raw image data.

(29) The method of any one of (14) to (20), wherein the medical image data is reconstructed image data.

(30) The method of any one of (14) to (20), wherein the medical image data is RF data.

In the preceding description, specific details have been set forth, such as a particular method and system for denoising ultrasound images using a neural network and descriptions of various components and processes used therein. It should be understood, however, that techniques herein may be practiced in other embodiments that depart from these specific details, and that such details are for purposes of explanation and not limitation. Embodiments disclosed herein have been described with reference to the accompanying drawings. Similarly, for purposes of explanation, specific numbers, materials, and configurations have been set forth in order to provide a thorough understanding. Nevertheless, embodiments may be practiced without such specific details. Components having substantially the same functional constructions are denoted by like reference characters, and thus any redundant descriptions may be omitted.

Various techniques have been described as multiple discrete operations to assist in understanding the various embodiments. The order of description should not be construed as to imply that these operations are necessarily order dependent. Indeed, these operations need not be performed in the order of presentation. Operations described may be performed in a different order than the described embodiment. Various additional operations may be performed and/or described operations may be omitted in additional embodiments.

Those skilled in the art will also understand that there can be many variations made to the operations of the techniques explained above while still achieving the same objectives of the invention. Such variations are intended to be covered by the scope of this disclosure. As such, the foregoing descriptions of embodiments of the invention are not intended to be limiting. Rather, any limitations to embodiments of the invention are presented in the claims.

The invention claimed is:

1. A medical image processing apparatus, comprising:

a memory storing at least one trained model for denoising medical image data;

processing circuitry configured to (1) obtain processed medical image data by normalizing noise characteristic information of the medical image data to resemble noise characteristic information of training data used for training a corresponding trained model of the at least one trained model, and (2) input the processed medical image data into the corresponding trained model to obtain output data; and display control circuitry configured to cause a display to display a medical image based on the obtained output data.

2. The apparatus of claim 1, wherein the at least one trained model for denoising medical image data stored in the memory comprises plural trained models, and the processing circuitry is further configured to choose the corresponding trained model from the plural trained models using system parameters of a system used to collect the medical image data.

3. The apparatus of claim 1, wherein the at least one trained model for denoising medical image data stored in the memory comprises plural trained models, and the processing circuitry is further configured to choose the corresponding trained model from the plural trained models using a pre-scanning of air by the apparatus.

4. The apparatus of claim 1, wherein the medical image processing apparatus is an ultrasound scanner.

5. The apparatus of claim 4, wherein the noise characteristic information is depth-specific noise information related to the ultrasound scanner.

6. The apparatus of claim 5, wherein the ultrasound scanner performs at least one of ultrasound B-mode imaging and Doppler ultrasound.

7. The apparatus of claim 1, wherein the medical image data is at least one of IQ data, RF data, and image data.

8. A medical image processing apparatus, comprising:

a memory storing a trained model generated by a machine-learning process based on first medical image data, noise characteristic information of the first medical image data, and second medical image data based on the first medical image data, the second medical image data having less noise than the first medical image data, the noise characteristic information indicating noise at each depth;

processing circuitry configured to input medical image data and the noise characteristic information of the medical image data into the trained model to obtain output data; and display control circuitry configured to cause a display to display a medical image based on the obtained output data.

9. The apparatus of claim 8, wherein the processing circuitry is further configured to obtain the noise characteristic information of the first medical image data by analyzing system parameters of a system used to collect the first medical image data.

10. The apparatus of claim 8, wherein the processing circuitry is further configured to obtain the noise characteristic information of the first medical image data by performing a pre-scanning scheme in a system used to collect the first medical image data.

11. A method, comprising:

obtaining processed medical image data by normalizing noise characteristic information of medical image data to resemble noise characteristic information of training data used for training a corresponding trained model from at least one trained model;

inputting the processed medical image data into the corresponding trained model to obtain output data; and displaying a medical image based on the obtained output data.

12. The method of claim 11, wherein the at least one trained model comprises plural trained models, and the method further comprises choosing the corresponding trained model from the plural trained models using system parameters of a system used to collect the medical image data.

13. The method of claim 11, wherein the at least one trained model comprises plural trained models, and the method further comprises choosing the corresponding trained model from the plural trained models by performing a pre-scanning of air.

14. The method of claim 11, wherein the noise characteristic information is depth-specific noise information related to an ultrasound scanner.

15. The method of claim 11, wherein the medical image data is obtained from an ultrasound scanner.

16. The method of claim 15, wherein the noise characteristic information is depth-specific noise information related to the ultrasound scanner.

17. The method of claim 15, wherein the ultrasound scanner performs at least one of Doppler ultrasound and ultrasound B-mode imaging.

18. The method of claim 11, wherein the medical image data is at least one of IQ data, RF data, and image data.

* * * * *